(12) United States Patent
Borg

(10) Patent No.: US 8,387,629 B1
(45) Date of Patent: Mar. 5, 2013

(54) ORTHODONTIC FLOSSER

(76) Inventor: N. Michelle Borg, Paradise, CA (US)

(*) Notice: Subject to any disclaimer, the term of this patent is extended or adjusted under 35 U.S.C. 154(b) by 233 days.

(21) Appl. No.: 12/904,058

(22) Filed: Oct. 13, 2010

Related U.S. Application Data

(60) Provisional application No. 61/251,609, filed on Oct. 14, 2009.

(51) Int. Cl.
*A61C 15/00* (2006.01)
(52) U.S. Cl. .................................................. 132/325
(58) Field of Classification Search ........... 132/323–328
See application file for complete search history.

(56) References Cited

U.S. PATENT DOCUMENTS

| | | | | |
|---|---|---|---|---|
| 1,306,998 A * | 6/1919 | Dimitroff | ...................... | 132/325 |
| 3,746,017 A * | 7/1973 | Casselman | ...................... | 132/325 |
| 4,706,694 A * | 11/1987 | Lambert | ...................... | 132/323 |
| 5,038,806 A * | 8/1991 | Ewald | ...................... | 132/325 |
| 5,184,631 A | 2/1993 | Ikeda | | |
| 5,495,683 A | 3/1996 | Miotto et al. | | |
| 5,678,578 A | 10/1997 | Kossak | | |
| 6,488,036 B1 | 12/2002 | Francis | | |
| 6,874,509 B2 | 4/2005 | Bergman | | |
| 7,011,099 B2 | 3/2006 | Bergman | | |
| 7,467,631 B2 | 12/2008 | Bergman et al. | | |
| 2002/0144705 A1* | 10/2002 | Brattesani et al. | ............ | 132/321 |
| 2009/0241984 A1* | 10/2009 | Wall | ............... | 132/323 |

* cited by examiner

*Primary Examiner* — Rachel Steitz
(74) *Attorney, Agent, or Firm* — Ron Rohde

(57) ABSTRACT

An orthodontic flosser comprising an elongated handle and an articulating head coupled to the handle at a pivot is disclosed. A mechanism holds the articulating head at a selected angle with respect to an axis of the handle. A first and second projection extend from the head for suspending floss, the first projection is sized to insert floss between a wire affixed to a tooth and the tooth. A supply of fresh floss and a take-up reel are configured to feed fresh floss incrementally into suspension between the first and second projections while taking-up used floss and applying a tension to the suspended floss.

14 Claims, 11 Drawing Sheets

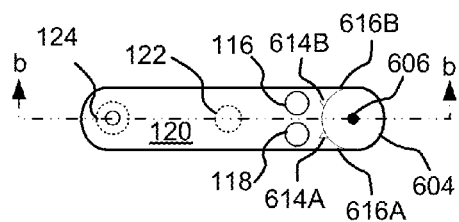 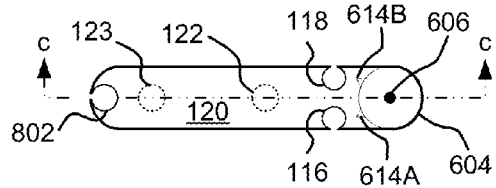
FIG. 7A                    FIG. 8A
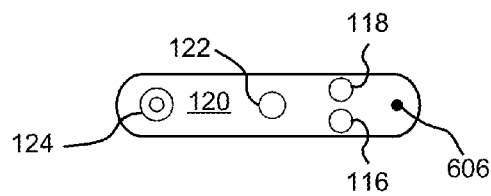 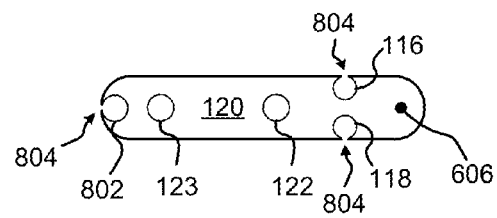
FIG. 7B                    FIG. 8B
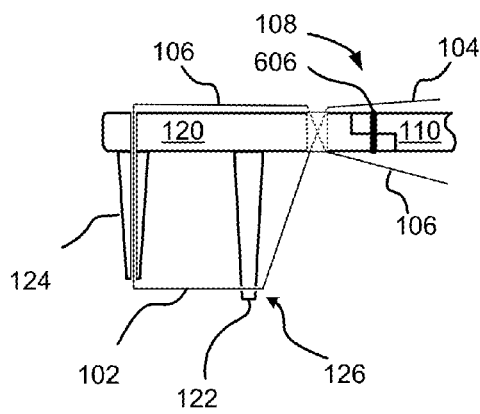 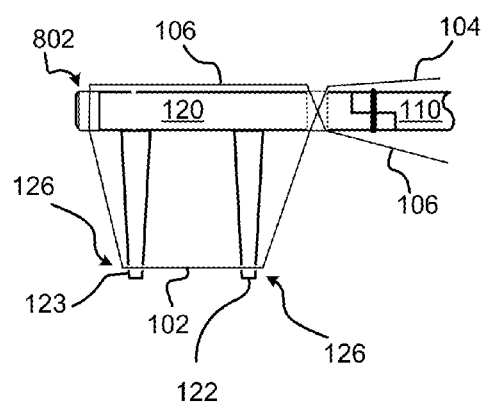
FIG. 7C                    FIG. 8C

ORTHODONTIC FLOSSER

CROSS-REFERENCE TO RELATED APPLICATIONS

The present application claims priority and benefit to U.S. provisional patent application Ser. No. 61/251,609 filed on Oct. 14, 2009 titled "ORTHODONTIC FLOSSER," and is related to U.S. provisional patent application Ser. No. 61/241,281, filed on Sep. 10, 2009 and titled "ANTI-MICROBIAL ORTHODONTIC FLOSS." Both of the above applications are incorporated by reference herein in their entirety.

BACKGROUND

1. Field of the Application

The present application relates generally to a flossing apparatus, and more particularly to an orthodontic flosser.

2. Description of Related Art

Flossing is particularly important for people who have braces. Braces typically include brackets bonded to the surfaces of two or more teeth and a wire or archwire affixed to the brackets. Flossing around braces may be accomplished by threading the floss between the braces and the teeth and then maneuvering a length of the floss into contacts between adjacent teeth. Upon flossing around a pair of teeth and braces, the floss must be pulled out and then threaded into another position for the next pair of teeth. Unfortunately, threading, inserting, manipulating the floss around the braces, and removing the floss for each pair of teeth can be difficult and time consuming. Maintaining tension on the floss while manipulating the floss between teeth and around braces involves a degree of dexterity and skill that is often beyond the ability of many children and even adults. Frustration due to the difficulty of acquiring skills, manipulating the floss, and the extra time required to thread and remove the floss can discourage flossing. The purpose of flossing is to remove particulate matter and bacteria from contacts between teeth and surfaces around braces to prevent interproximal tooth decay and gum disease. Unfortunately, floss can pick up bacteria from surfaces of the teeth and the braces in the process. The floss can then distribute the bacteria to other teeth and braces around the mouth, thus further spreading tooth decay and gum disease.

SUMMARY

A flosser employing embodiments of the technology includes a handle attached to a projection that supports suspended floss. The projection is sized and shaped for insertion between an arch wire and a contact between two teeth connected to the arch wire. The size and shape of the projection simplify insertion of the floss secured to the end of the projection between the teeth and wire to make flossing the contacts faster and easier. Floss that is suspended parallel to the handle can be difficult to manipulate around molars in the back of the mouth. The floss may be suspend at an angle with respect to the axis of the handle to reduce the difficulty of flossing rear molars. An articulating head that supports the projection may be connected to the handle and rotated to change the angle of the suspended floss from an angle for reaching molars on the right side to an angle for reaching the molars on the left side. Fresh floss may be periodically advanced into suspension on the projection by a mechanism that holds the suspended floss under tension. Using fresh floss to clean each contact helps prevent spreading of microbes around the mouth and braces. Impregnating the floss with an antimicrobial agent further helps control the spread of microbes.

Various embodiments of the technology include a flosser having an elongated handle and an articulating head coupled to the handle at a pivot. A first detent holds the articulating head at a first angle with respect to an axis of the handle and a second detent holds the head at a second angle with respect to the axis. A first and second projection extend from the head for suspending floss, the first projection is sized for insertion between a wire affixed to a pair of teeth and contact formed between the teeth. A source provides fresh floss to feed through an aperture in the first projection for suspension between the first and second projections. A take-up apparatus draws the floss through the flosser and maintains tension on the floss.

Various embodiments of the technology include a flosser for cleaning contacts between two teeth that are attached to a wire brace. The flosser includes a handle, and a head coupled to the handle at an angle. A first floss support may be coupled to the head and extend away from a plane formed by the angle between the head and the handle. A second floss support may extend from the head about parallel to the first floss support and include an aperture for supporting floss suspended between the first floss support and the second floss support. The second floss support may be shaped for insertion of the aperture between the wire brace and the two teeth while the suspended floss cleans the contact between the two teeth. A source spool may be disposed on the handle for dispensing fresh floss. The aperture may be sized for feeding the fresh floss into suspension between the first and second floss support. A take-up spool may be disposed on the handle for receiving used floss from the first floss support and for advancing the fresh floss through the aperture, the take-up spool and the source spool may be configured to apply tension to the suspended floss. The floss may be impregnated with an antimicrobial agent.

Various embodiments of the technology include a method for flossing a contact between two teeth that are attached to a wire brace, the method including dispensing fresh floss from an elongated handle and suspending the fresh floss at an angle to the elongate handle between a pair of projections while applying a tension to the suspended fresh floss. The method further includes inserting one of the projections between the teeth and the wire brace while flossing the contact using the suspended fresh floss. The method also includes advancing fresh floss into suspension between the pair of projections while collecting used floss and maintaining the tension on the suspended floss.

BRIEF DESCRIPTION OF THE DRAWINGS

FIG. 7A is a top plan view of the head of FIG. 1.

FIG. 7B is a bottom plan view of the head of FIG. 7A.

FIG. 7C is a cross section of the head of FIG. 7A taken along the line b-b of FIG. 7A.

FIG. 8A is a top plan view illustrating an alternative embodiment of the head of FIG. 1.

FIG. 8B is a bottom plan view of the head of FIG. 8A.

FIG. 8C is a cross section of the head of FIG. 8A taken along the line c-c of FIG. 8A.

DETAILED DESCRIPTION

Figure 1:
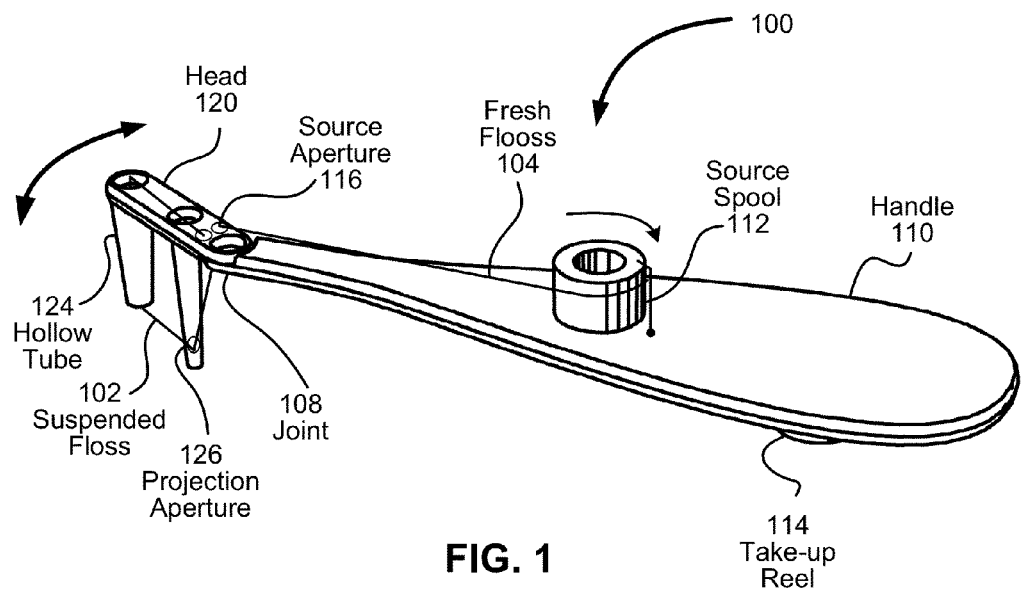
FIG. 1 is a top perspective view of an embodiment of a flosser, in accordance with aspects of the technology.
Figure 2:
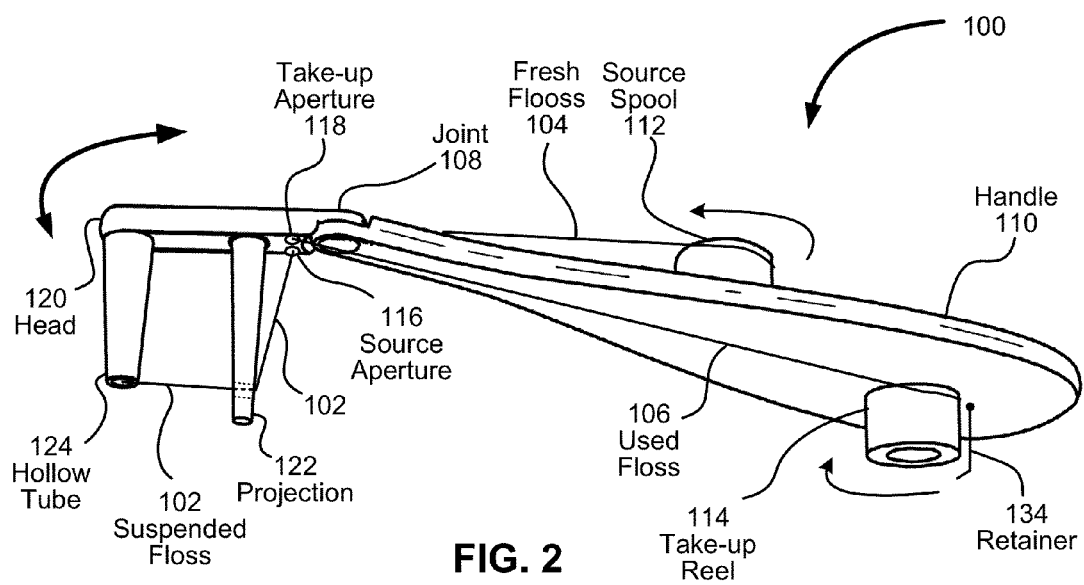
FIG. 2 is a bottom perspective view the flosser of FIG. 1

FIG. 1 is a top perspective view of an embodiment of a flosser 100, in accordance with aspects of the technology. FIG. 2 is a bottom perspective view of the flosser 100 of FIG. 1. The flosser 100 includes a handle 110 and a head 120. The handle 110 supports a source spool 112 for dispensing fresh floss 104 and a take-up reel 114 collecting used floss 106. The head 120 of FIG. 1 includes a projection 122 and a hollow tube 124 that are configured for supporting suspended floss 102. Grooves, channels, and apertures may be disposed along the handle 110 and the head 120 for routing and guiding fresh floss 104 and/or used floss 106. A support aperture or projection aperture 126 may be disposed near the tip of the projection 122. The floss 102 may be suspended between the tube 124 and the support aperture 126 in the projection 122. The support aperture 126 is configured to support the floss 102 near the tip of the projection 122.

The floss 102-106 of FIGS. 1 and 2 is routed along the handle and head from the source spool 112, into suspension between the projection 122 and the hollow tube 124, and to the take-up reel 114. In one example, the fresh floss 104 is dispensed from the source spool 112, threaded through a source aperture 116, threaded through the support aperture 126 in the projection 122, threaded through the tube 124, threaded through the take-up aperture 118, and received at the take-up reel 114 as used floss 106. The take-up reel 114 is configured to apply tension to the used floss 106. The source spool 112 is configured to resist the tension applied to the used floss 106 by the take-up reel 114, while dispensing fresh floss 104. Thus, the source spool 112 and the take-up reel 114 may co-operate to maintain tension on the floss 102 that is suspended between the tube 124 and the projection 122. The source spool 112 and/or the take-up reel 114 may be supported on the handle 110 using a post (illustrated elsewhere herein). An optional retainer 134 may be used for preventing the source spool 112 and/or the take-up reel 114 from falling off the handle 110 during use.

The head 120 of FIGS. 1 and 2 is configured to articulate on the handle. The head 120 may be urged into a position at one or more angles with respect to the handle 110. For example, a detent illustrated elsewhere herein may hold the head 120 at a first angle with respect to the handle 110, inline with the handle 110, and/or at a second angle with respect to the handle 110. Alternatively, the head 120 may be urged into a first or second angle with respect to the handle 110 using a resilient component.

Antimicrobial agents may be infused into the floss 102-106 for inhibiting transfer of bacteria between surfaces of teeth, braces, and from one contact to another. For example, the floss 102-106 may be permeated with chlorhexidine gluconate to inhibit survival of bacterial and other microbes in the floss 102 during use and to inhibit deposition of microbes on the surfaces of teeth, contacts, and/or braces. Various antimicrobial agents include chlorhexidine gluconate, hydrogen peroxide, carbamide peroxide, and cetylpyridinium chloride. Environmentally friendly antimicrobial agents may be used, including an extract of magnolia bark, xylitol (a sugar alcohol that is naturally occurring in Birch and fruits), and antimicrobial peptides, which are compounds that are found throughout the animal and plant kingdom such as HNP (human neutrophil proteins). The floss 102-106 may also be infused with anti-cavity agents such as florides, e.g., sodium fluoride, hexafluorosilicic acid ($H_2SiF_6$) and its salt sodium hexafluorosilicate ($Na_2SiF_6$), and/or the like. The floss 102 may also be used for depositing the antimicrobial and/or anti-cavity agents on the surfaces of teeth and/or braces. In some embodiments, the antimicrobial agent may be applied to the fresh floss 104 as the fresh floss 104 is dispensed from the source spool 112 during use. For example, the fresh floss 104 may be routed through a reservoir of antimicrobial agent disposed on the handle 110. The reservoir may be configured to apply the antimicrobial agent to the fresh floss 104 during transit. The above antimicrobial and anti-cavity agents may be used individually or in various combinations and mixtures.

Figure 3:
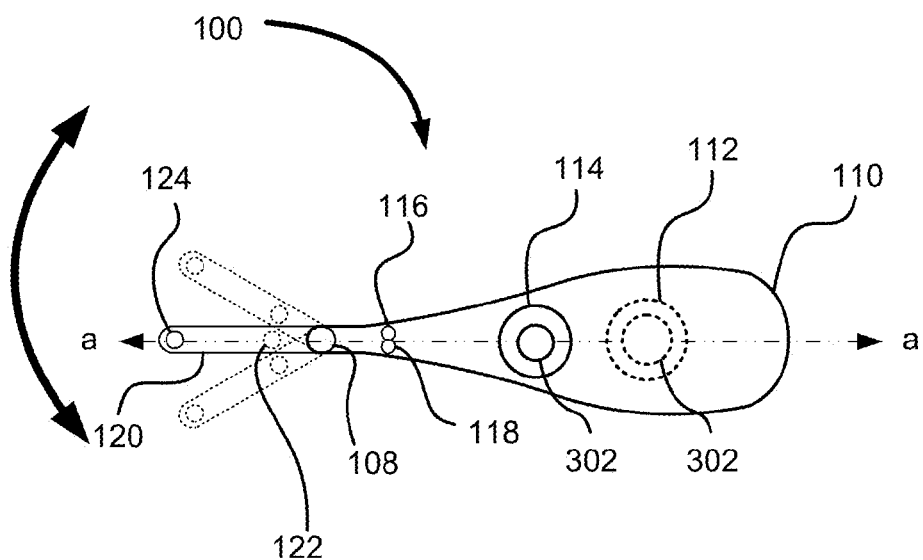
FIG. 3 is a top plan view of the flosser of FIG. 1.

FIG. 3 is a top plan view of the flosser 100 of FIG. 1. The floss 102-106 is omitted for clarity. The head 120 may be positioned at various angles with respect to the handle 110 during use for ease of flossing. FIG. 3 illustrates articulation of the head 120 about the joint 108. The head 120 shown in solid lines indicates a position about parallel to, or in-line with, an axis of the handle 110. The head 120 is also shown in broken lines to indicate articulation. The broken lines indicate alternative positions of the head 120 that may be selected during use. A longitudinal axis of the handle 110 may be defined as a line coincident with line a-a. The take-up reel 114 and a post 302 are shown in broken lines to indicate that they are on the opposite side of the handle 110 from the viewer.

Figure 4:
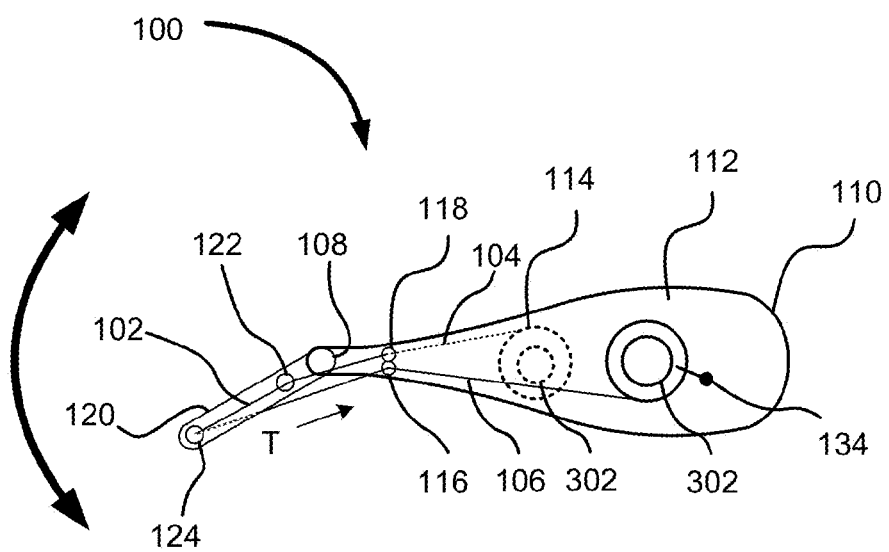
FIG. 4 is a bottom plan view of the flosser of FIG. 1.

FIG. 4 is a bottom plan view of the flosser 100 of FIG. 1. The head 120 is illustrated as deflected at an angle from the longitudinal axis of the handle 110. The fresh floss 104 from the source spool 112 is shown as threaded through the source aperture 116, the projection aperture 126, the tube 124, and the take-up aperture 118, and attached to the take-up reel 114 as used floss 106. The source aperture 116 and the take-up aperture 118 are illustrated in FIGS. 3 and 4 as being disposed in the handle 110 instead of the head 120 as illustrated in FIGS. 1 and 2. In some embodiments, the source aperture 116 may be disposed in the handle 110 and the take-up aperture 118 may be disposed in the head, or vice versa. An aperture disposed in the handle 110 may be useful for applying a tension T through the fresh floss 104 and/or the used floss 106 for rotating the head 120 to an angle with respect to the handle 110. A torque applied by the tension T may further serve to hold the rotated head 120 against a stop or in a detent. In another embodiment, a single aperture may be used for both the source aperture 116 and the take-up aperture 118. The single aperture may be disposed in either the handle 110 or the head 120. The take-up reel 114 and portions of the floss 102-106 are shown in broken line to indicate that they are on the opposite side of the handle 110 from the viewer.

Figure 5:
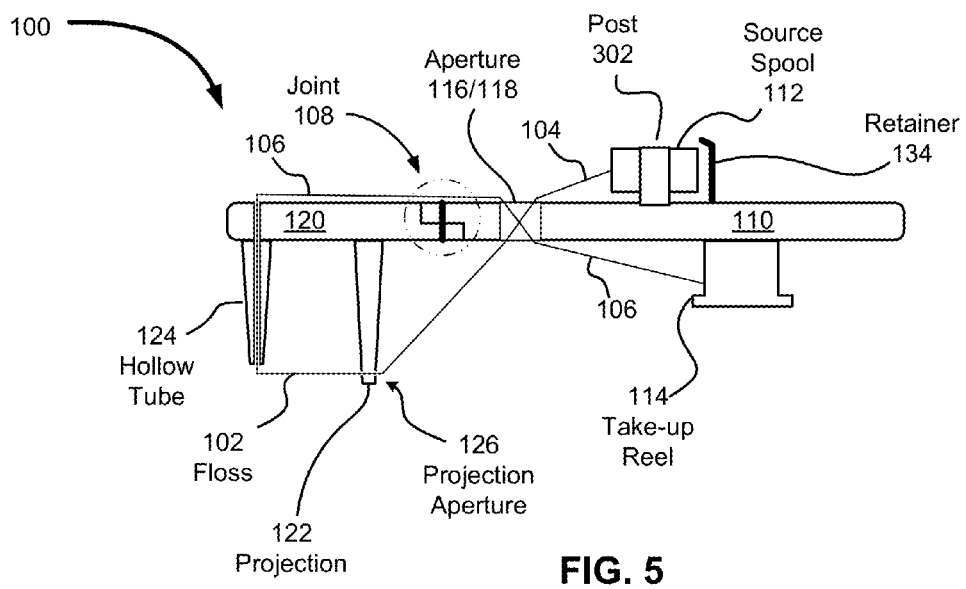
FIG. 5 is a side cross section of the flosser of FIG. 3 taken through line a-a.

FIG. 5 is a side cross section of the flosser 100 of FIG. 3 taken through line a-a. FIG. 5 illustrates a path for the floss 102-106. The source and take-up apertures are illustrated in FIG. 5 as being a single aperture 116/118 disposed in the handle. As in FIG. 4, the fresh floss 104 from the source spool 112 is shown as threaded through the aperture 116/118, the projection aperture 126, the tube 124, back through the aperture 116/118, and attached to the take-up reel 114 as used floss 106.

In FIGS. 1-5, the take-up reel 114 is illustrated as disposed on the bottom of the handle 110 and the source spool 112 is illustrated as disposed on the top of the handle 110. However, the take-up reel 114 may be disposed on the top, the bottom, the side, the rear, or the inside of the handle 110. Similarly, the source spool 112 may be disposed on the top, the bottom, the side, the rear, or the inside of the handle 110. The source spool 112 and the take-up reel 114 may be disposed on the same surface or different surfaces.

In FIGS. 1-5, the floss 102-106 is illustrated as routed from source spool 112 though the projection aperture 126 to the bottom of the tube 124 and then from the top of the tube 124 to the take-up reel 114, via the various apertures. However, the floss 102-106 may alternatively be routed from source spool 112 through the tube 124 to the projection aperture 126 and then from the projection aperture 126 to the take-up reel 114 via the various apertures.

Figure 6A:
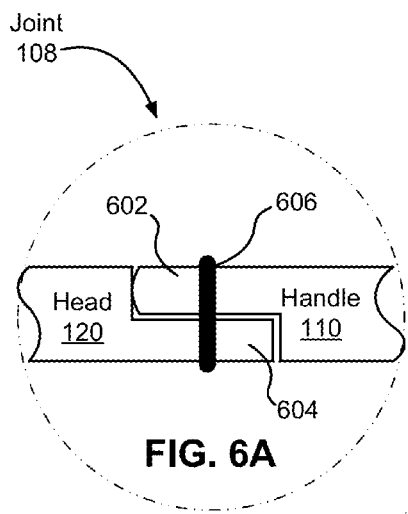
FIG. 6A is an enlargement of the joint of FIG. 5 illustrating details of the joint.

FIG. 6A is an enlargement of the joint 108 of FIG. 5 illustrating details of the joint 108. The joint 108 of FIG. 6 includes an upper flange 602, a lower flange 604 and a pin 606. The pin 606 is configured to secure the lower flange 604 of the head 120 to the upper flange 602 of the handle 110 and provide for pivoting of the head 120 with respect to the handle 110. The upper flange 602 of FIG. 6A is a component of the handle 110 and the lower flange 604 is a component of the head 12. However, the upper flange may be a component of the head 120 and the lower flange may be a component of the handle 110.

Figure 6B:
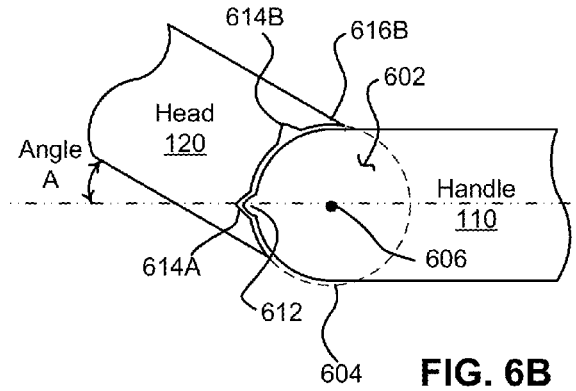
FIG. 6B and FIG. 6C are top plan views of the joint of FIG. 6 illustrating details of an example of a detent assembly.
Figure 6C:
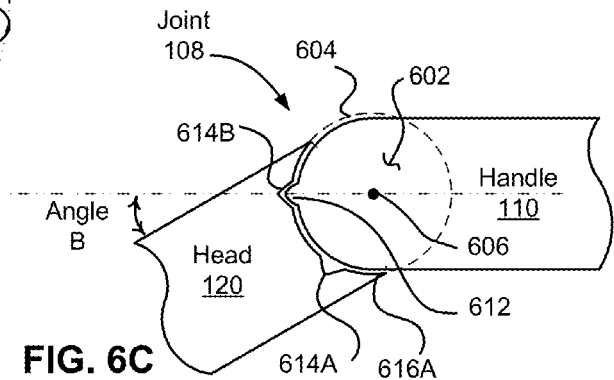

FIG. 6B and FIG. 6C are top plan views of the joint 108 of FIG. 6 illustrating details of an example of a detent assembly. The detent assembly of FIGS. 6A and 6B comprises a catch 612 disposed in the handle 110 and two notches 614, namely a first notch 614A and a second notch 614B disposed in the head 120. The catch 612 may comprise a resilient material configured for elastic deformation. In FIG. 6B, the catch 612 engages the first notch 614A to hold the head 120 above longitudinal axis at an angle A of about 30 degrees with respect to the handle 110. In FIG. 6C, the catch 612 engages the second notch 614B to hold the head 120 below the longitudinal axis at an angle B of about −30 degrees with respect to the handle 110. In some embodiments the notches 614 are disposed in the handle 110 and the catch 612 is disposed in the head 120.

FIGS. 6B and 6C illustrate an example of two notches 614 and two positions for the detent of the joint 108. However, in various embodiments, multiple notches 614 may provide 3, 4, 5, 6, 7, 8, or more positions. FIGS. 6B and 6C illustrate angles of about plus and minus 30 degrees, respectively, for deflection of the head 120 from an alignment with the longitudinal axis of the handle 110. However, the angle A may be any angle between 5 degrees and 90 degrees above the longitudinal axis of the handle 110 and the angle B may be any angle between 0 and −90 degrees, that is, below the longitudinal axis of the handle 110. For example, the angles A and/or B may be about 0, 5, 10, 15, 20, 25, 30, 35, 40, 45, 50, 55, 60, 65, 70, 75, 80, 85, or 90 degrees or more above or below the longitudinal axis.

FIGS. 6B and 6C illustrate detents for holding the head 120 at a desired angle with respect to the handle 10. However, other mechanisms may be used. For example, the head 120 may pivot about the joint 108 and a resilient material such as elastic or springs may be used to urge the head 120 away from a center position in alignment with the handle 110. The elastic material may be used to hold the head 120 against stops, such as stops 616A and 616B, on either side of the axis of the handle 110.

FIG. 7A is a top plan view of the head 120 of FIG. 1. FIG. 7B is a bottom plan view of the head 120 of FIG. 7A. The source aperture 116 and the take-up aperture 118 of FIGS. 7A and 7B are disposed in the head 120. The top and bottom positioning of the source aperture 116 and the take-up aperture 118, respectively, is arbitrary and may be reversed. The floss 102-106 is omitted from FIGS. 7A and 7B for clarity.

FIG. 7C is a cross section of the head 120 of FIG. 7A taken along the line b-b of FIG. 7A. FIG. 7C includes a portion of the handle 110. FIG. 7C illustrates routing of the suspended floss 102 through the tube 126 and the projection aperture 126. The floss 102 is suspended between the tube 124 and the support projection 122. The projection aperture 126 is illustrated as about the same distance from the head 120 as the end of the tube 124, resulting in the suspended floss being about parallel to the head 120. However, the projection aperture 126 may be closer or farther from the head than the end of the tube 124 resulting in an angle between the suspended floss 102 and the head 120.

FIG. 8A is a top plan view illustrating an alternative embodiment of the head 120 of FIG. 1. FIG. 8B is a bottom plan view of the head 120 of FIG. 8A. The floss 102-106 is omitted from FIGS. 8A and 8B for clarity. FIG. 8C is a cross section of the head 120 of FIG. 8A taken along the line c-c of FIG. 8A. FIG. 8C includes a portion of the handle 110. FIGS. 8A-C differ from FIGS. 7A-C in that FIGS. 8A-C include a second projection 123 instead of the tube 124 of FIGS. 7A-C. Further FIGS. 8A-C include a tip aperture 802 instead of the bore of the tube 124. The tip aperture 802 includes an optional cut or groove 804 from the interior and of the tip aperture 802 to the exterior of the head 120. Similarly, the source aperture 116 and the take-up aperture 118 include an optional groove 804. The groove 804 permits a length of the floss 102-106 to be inserted into the respective apertures from the side without the need to thread an end of the floss 102-106 through the apertures. The grooves 804, thus, simplify installing the floss 102-106 on the flosser 100. In some embodiments, a groove, such as a V-groove, may be used instead of the tip aperture 802.

FIG. 8C illustrates routing of the floss 102-106 through the head 120. The floss 102 is suspended between the two projection apertures 126 of the projection 122 and the projection 123. Tension on the floss 102-106 maintains the floss within the various apertures 116, 118, and/or 802 and prevents the floss 102-106 from slipping out through the grooves 804. The projection 122 and the projection 123 of FIG. 8C are of about equal length, thus, suspending the floss 102 about parallel to the head 120. However, the projections 122 and 123 may be of different lengths, thus, suspending the floss 102 at a verticle angle with respect to the head 120. Either projection 122 or 123 may be longer than the other. Either of the projections 122 or 123 may be inserted into a space between a wire attached to a pair of teeth and a contact between the teeth. Thus, the projection 122 may be used for flossing between a wire and a tooth that cannot be conveniently reached by the projection 123. Conversely, the projection 123 may be used for flossing between a wire and a tooth that cannot be conveniently reached by the projection 122.

Figure 9A:
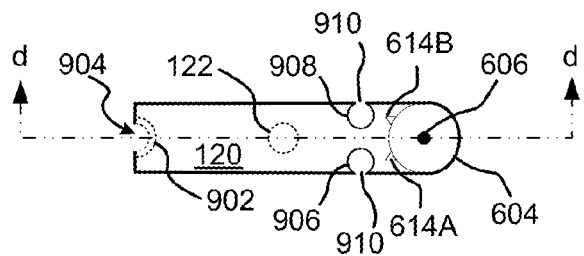
FIG. 9A is a top plan view illustrating an alternative embodiment of the head of FIG. 1.
Figure 9D:
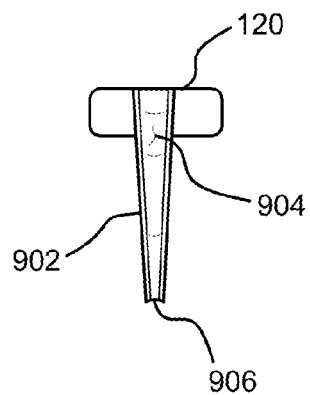
FIG. 9D is a front elevation of the head of FIG. 9A.
Figure 9B:
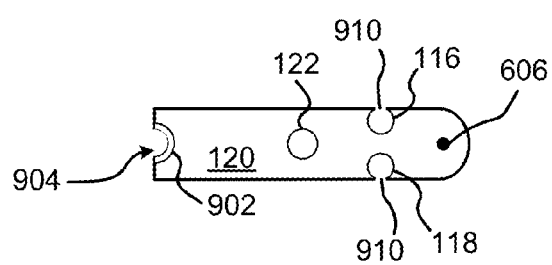
FIG. 9B is a bottom plan view of the head of FIG. 9A.
Figure 9C:
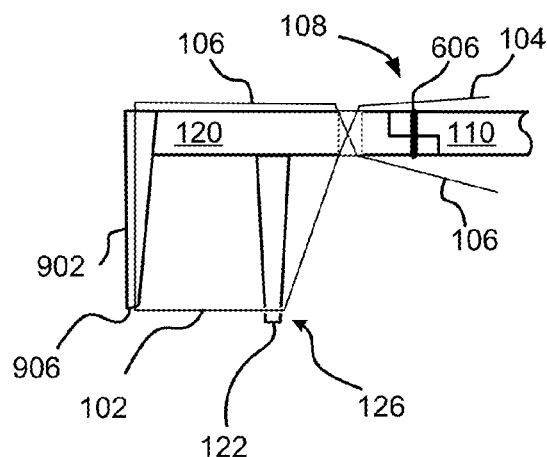
FIG. 9C is a cross section of the head of FIG. 9A taken along the line d-d.

FIG. 9A is a top plan view illustrating an alternative embodiment of the head 120 of FIG. 1. FIG. 9B is a bottom plan view of the head 120 of FIG. 9A. FIG. 9C is a cross section of the head 120 of FIG. 9A taken along the line d-d. FIG. 9D is a front elevation of the head 120 of FIG. 9A. The head 120 of FIGS. 9A-D differs from the head 120 of FIG. 1 in that the head 120 of FIGS. 9A-D includes a projection 902 instead of the tube 124. The projection 902 includes a channel, trough, or groove 904 disposed along the length of the projection 902. The groove 904 is configured to guide the floss 102-106. A length of floss 102-106 may be placed in the groove 904 instead of threaded through the tube 124. The floss 102 is suspended between a tip 906 of the projection 902 and the projection aperture 126. Tension on the suspended floss 102 may constrain the floss 102-106 within the groove 904. The head 120 of FIGS. 9A-D includes grooves 910 instead of a source aperture and a take-up aperture. The grooves 910 include curved sides to help retain the floss 102-106 within the grooves while under tension. A length of floss 102-106 may be inserted into the grooves 910 instead of being threaded through an aperture. The grooves 904 and 910, thus, serve to simplify routing of the floss 102-106. Floss 102-106 is omitted from FIGS. 9A, 9B and 9D for clarity. Fresh floss 104 from the source spool and used floss 106 from the take-up reel may be disposed in either groove 910.

Figure 10B:
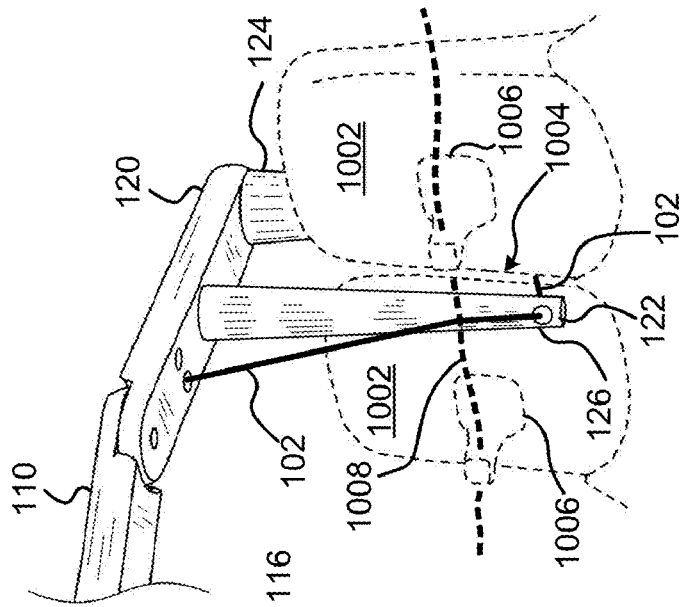
FIG. 10B is a partial perspective view of a block diagram illustrating use of the flosser with the head articulated to the left.
Figure 10A:
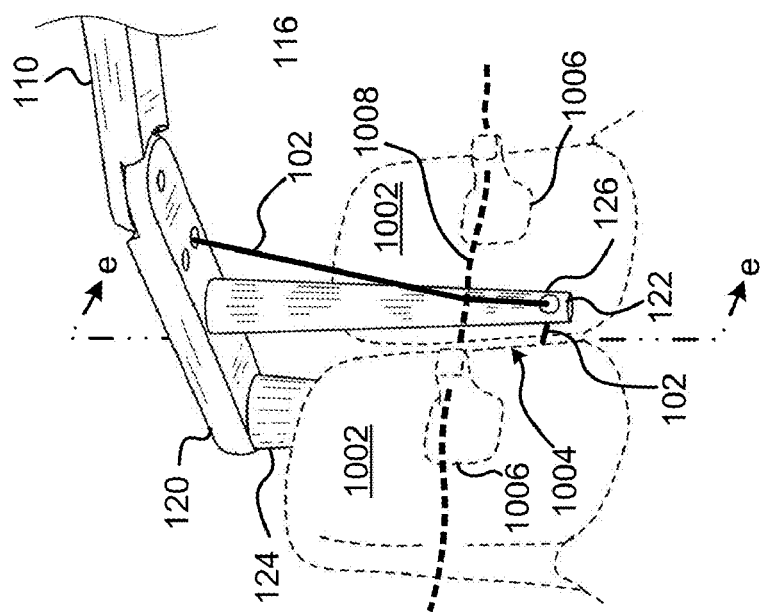
FIG. 10A is a partial perspective view of a block diagram illustrating use of the flosser with the head articulated to the right.

FIG. 10A is a partial perspective view of a block diagram illustrating use of the flosser 100 with the head 120 articulated to the right. FIG. 10B is a partial perspective view of a block diagram illustrating use of the flosser 100 with the head 120 articulated to the left. FIG. 10A provides an external view of two adjacent teeth 1002. A contact 1004 is the space between the two teeth 1002. Other teeth and portions of the mouth are omitted for clarity. A bracket 1006 is affixed to each of the teeth 1002. A wire 1008 is attached to the brackets. The brackets 1006 and the wire 1008 are components of braces used for altering the relative positions and/or orientation of the teeth 1002. Other components of the braces are omitted for clarity. As can be seen, the wire 1008 interferes with normal flossing of the contact 1004, particularly flossing of the portion of the contact 1004 below the wire 1008.

The projection 122 simplifies flossing the portions of the contact 1004 that are below the wire 1008. The projection 122 is sized and shaped for insertion between the wire 1008 and the contact 1004. The projection 122 simplifies positioning of the aperture 126 and suspended floss 102 below the wire 1008. Thus, the floss 102 suspended between the projection 122 and the tube 124 may be easily applied to the portions of the contact 1004 that are below the wire 1008. The tube 124 supports the floss on the interior side of the teeth 1002 during use. The projection 122 and the tube 124 straddle the teeth 1002 and contact 1004.

In some embodiments, floss 102 that is suspended between the aperture 126 and the source aperture 116 may engage the wire 1008 and/or brackets 1006 for cleaning surfaces of components of the braces. The teeth 1002, brackets 1006, and wire 1008 in FIG. 10A are illustrated in block diagram form show relative positions and represent a variety of shapes and sizes.

The angle of the head 120 with respect to the handle 110 permits easier flossing of teeth along the side of the mouth. For example, consider the case where the teeth 1002 illustrated in FIG. 10A are right rear lower molars. The angle of the head 120 in FIG. 10A is to the right as seen from the top of the flosser 100. The angle of the head 120 to the right permits easier manipulation of the head 120 using the handle 110 from the front of the mouth.

Alternatively, consider the case where the teeth 1002 illustrated in FIG. 10B are the left rear lower molars. The head 120 may be rotated to an angle on the left as illustrated in FIG. 10B. The angle of the head 120 to the left permits easier manipulation of the head 120 around the left rear lower molars of FIG. 10B. A handle that is inline with the head could cause uncomfortable distension of the cheeks around the teeth 1002. Thus, the angle of the head 120 may improve the comfort and ease with which the flosser 120 is used.

Figure 10C:
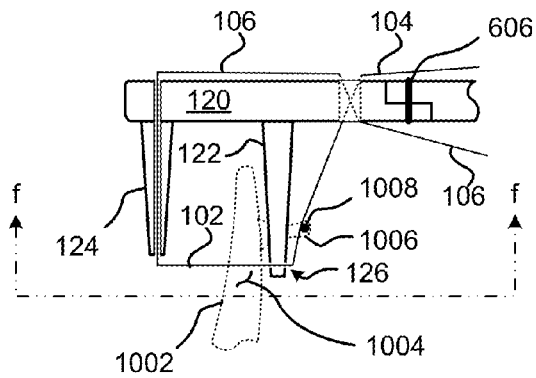
FIG. 10C is a cross section of head of FIG. 10A taken along line e-e of FIG. 10A.

FIG. 10C is a cross section of head 120 of FIG. 10A taken along line e-e of FIG. 10A. The cross section is a plane that includes line e-e and the axis of the head 120. For clarity, only one of the tooth 1002 is shown in FIG. 10. The projection 122 and the tube 124 are shown straddling the tooth 1002. The aperture 126 is below the wire 1008. The floss 102 suspended between the tube 124 and the aperture is also below the wire 1008. The portion of the floss that is suspended between the aperture 126 and the source aperture 116 may be seen bearing against the wire 1008 and providing flossing action of the wire 1008.

Figure 10E:
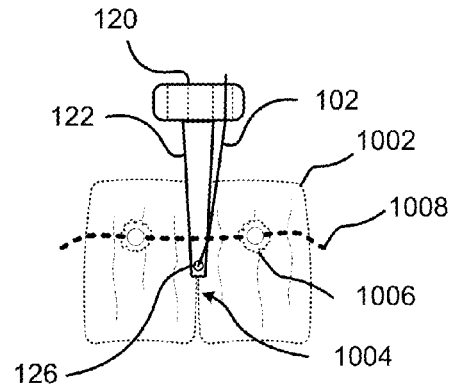
FIG. 10E is a cross section taken along line g-g of FIG. 10D.
Figure 10D:
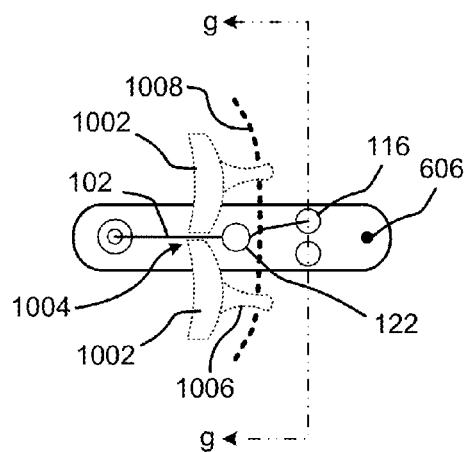
FIG. 10D is a cross section taken along line f-f of FIG. 10C.

FIG. 10D is a cross section taken along line f-f of FIG. 10C. The cross section of FIG. 10D cuts through a portion of the teeth 1002 and the view is from the teeth 1002 looking up toward the head 120. Thus, FIG. 10D represents a bottom plan view of the head 120, as well as the brackets 1006 and the wire 1008. FIG. 10E is a cross section taken along line g-g of FIG. 10D. The cross section of FIG. 10E cuts through the source aperture 116.

Figure 11A:
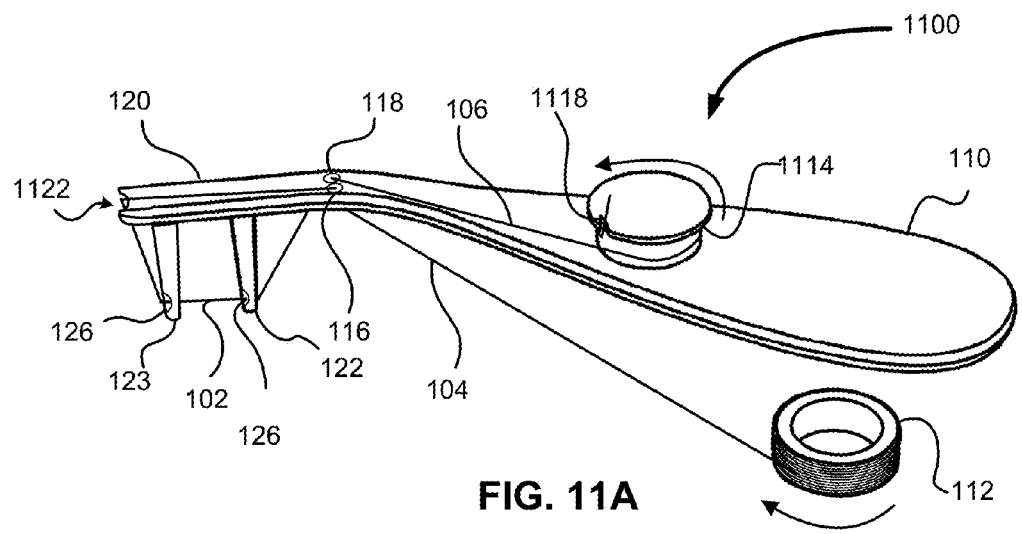
FIG. 11A is a top perspective view of an alternative embodiment of a flosser, in accordance with aspects of the technology.
Figure 11B:
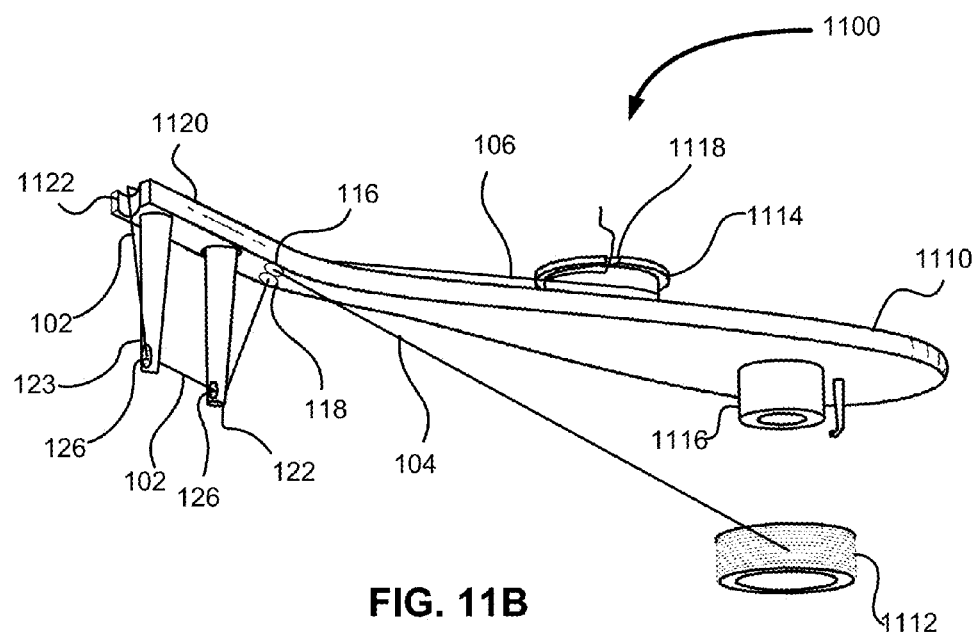
FIG. 11B is a bottom perspective view of the flosser of FIG. 11A.

FIG. 11A is a top perspective view of an alternative embodiment of a flosser 1100, in accordance with aspects of the technology. FIG. 11B is a bottom perspective view of the flosser 1100 of FIG. 11A. The flosser 1100 includes a head 1120 at a fixed angle with respect to the handle 1110. The angle of the head 1120 is fixed with respect to the handle 110 and is not configured for articulation. In FIG. 11, a take-up reel 1114 is disposed on the top surface. A source spool 1112 is disposed on the bottom of the handle 1110. The source spool 1112 is shown suspended below a post 1116 for purposes of illustration. In normal use, the source spool 1112 is disposed on the post 1116. A take-up reel 1114 is disposed on the top of the handle 1110. A notch disposed in the take-up reel 1114 may be used for securing the used floss 106. The take-up reel 1114 may be disposed on the top, the bottom, the side, or rear of the handle 1110. Similarly, the source spool 1112 may be disposed on the top, the bottom, the side, or rear of the handle 1110. The source spool 1112 and the take-up reel 1114 may be disposed on the same surface.

A second projection 123 is disposed on the head 1120. The second projection 123 may be identical to the first projection 122. The floss 102-106 may be routed through a groove 1122 that is configured to hold the floss 102-106 under tension at the end of the head 1120. In some embodiments, an aperture is used in place of the groove 1122, for example, the aperture 802 as described in FIGS. 8A-C. The second projection 123 may be used between the wire of a brace and the contact between two teeth instead of the first projection 122 depending on the position and orientation of the various teeth. The choice of using either the first projection 122 or the second projection 123 may simplify accessing contacts between teeth such as back molars. Thus, the projection 122 may be used for flossing a tooth that cannot be easily reached by the projection 123. Similarly, the projection 123 may be used for flossing a tooth that cannot be easily reached by the projection 122. In various embodiments, the angle between the head 1120 and the handle 1110 is about 5, 10, 15, 20, 25, 30, 35, 40, 45, 50, 55, 60, 65, 70, 75, 80, 85, or 90 degrees or greater.

Figure 12A:
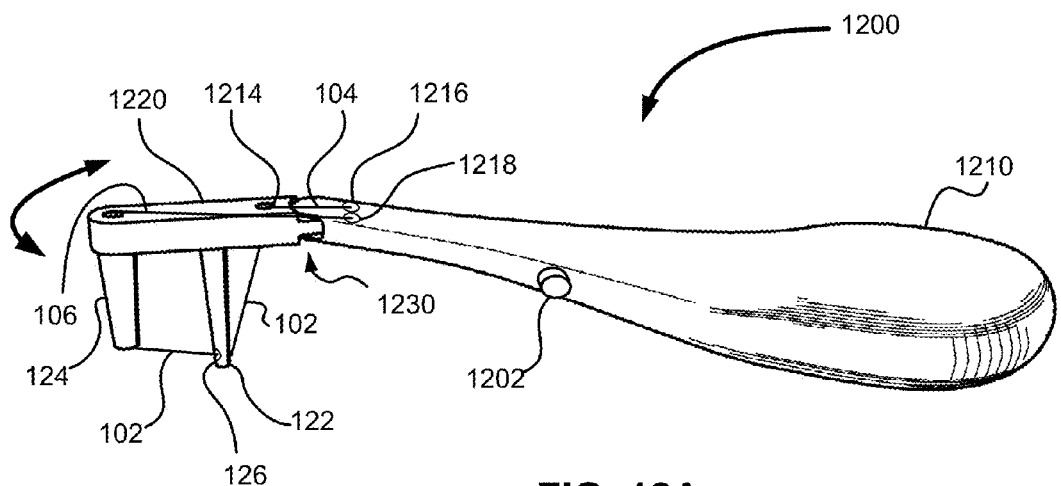
FIG. 12A is a top perspective view of an alternative embodiment of a flosser, in accordance with aspects of the technology.
Figure 12B:
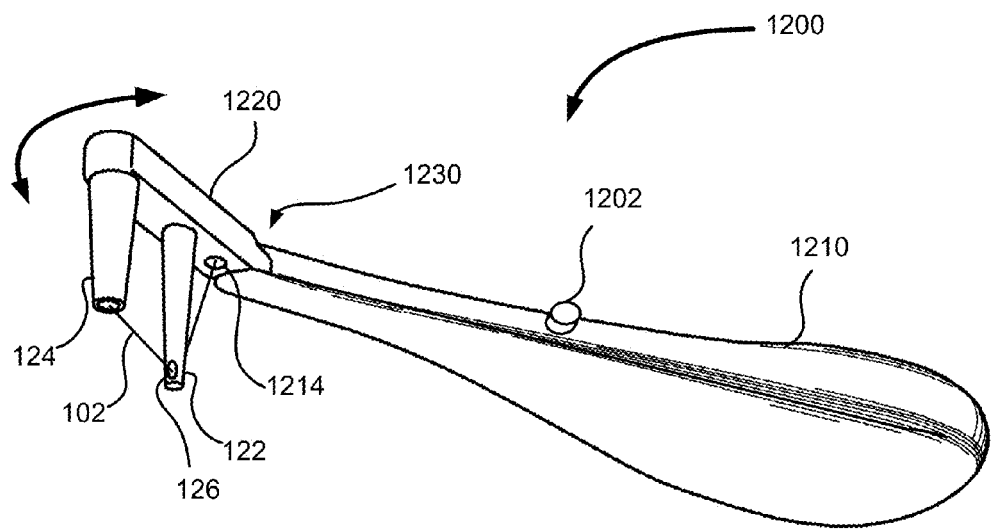
FIG. 12B is a bottom perspective view of the flosser of FIG. 12A.

FIG. 12A is a top perspective view of an alternative embodiment of a flosser 1200, in accordance with aspects of the technology. FIG. 12B is a bottom perspective view of the flosser 1200 of FIG. 12A. The flosser 1200 comprises a handle 1210 and a head 1220. The handle 1210 may be constructed using an outer shell to contain a source spool and a take-up reel (not shown) as well as other apparatus for dispensing fresh floss 104 and maintaining tension on the floss 102-106. A source aperture 1216 provides an exit for the fresh floss 104 from the handle 1210. A routing aperture 1214 disposed in the head 1220 may provide for routing the fresh floss 104 from the source aperture 1216 through the head 1220 to the projection aperture 126. A joint 1230 may be used for articulation of the head 1220.

A button 1202 may be pressed for advancing the floss 102-106. The button 1202 may rotate the take-up reel in increments against tension applied by the source spool. A ratchet may hold the take-up reel against reverse rotation. Thus, each press of the button 1202 may advance an incremental length of fresh floss 106 into suspension between the projection 122 and the tube 124 to become suspended floss 102. The head 1220 may include various components described elsewhere herein. For example, a second projection 123 or a grooved projection maybe used instead of the tube 124. Grooves may be disposed in apertures for routing floss 102-106. The joint 1230 may include a detent. The joint 1230 illustrated in FIGS. 12A and 12B includes a tongue and groove type of joint. However, other forms of joint may be used for joint 1230.

In some embodiments, the flosser 1200 may be used as a disposable flosser. That is, a length of fresh floss 104 may be loaded into the handle 1210 sufficient for a period of time under typical use, e.g., 1 month, 3 months, 6 months, one year, and etc. The shell comprising the handle 1210 may be permanently closed during manufacturing such that the flosser 1200 cannot be reloaded with fresh floss 104 when the floss is completely used. In another embodiment, an antimicrobial reservoir may be disposed inside the handle 1210. The antimicrobial agent in the reservoir may be applied to the fresh floss 104 as it is dispensed from the handle for use. For example, the fresh floss 104 may be routed through the reservoir. The reservoir may be configured to apply the antimicrobial agent to the fresh floss 104 during transit. Flosser 100 and flosser 1100 may similarly be configured as disposable flosser and include antimicrobial application.

Figure 13A:
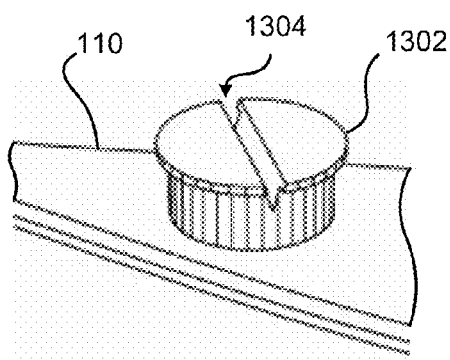
FIG. 13A is a partial perspective view illustrating details of an exemplary take-up reel.
Figure 13B:
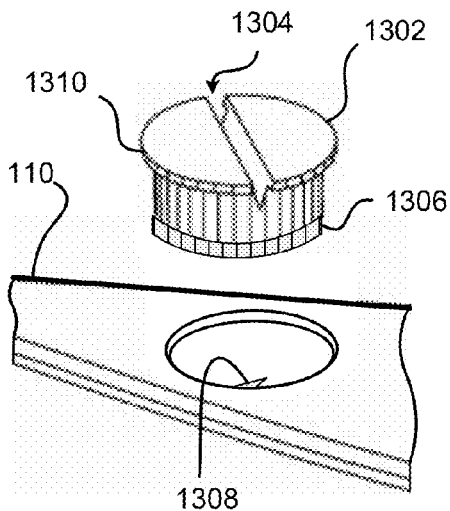
FIG. 13B is an exploded perspective view of the take-up reel of FIG. 13A.

FIG. 13A is a partial perspective view illustrating details of an exemplary take-up reel 1302. FIG. 13B is an exploded perspective view of the take-up reel 1302 of FIG. 13A. The take-up reel 1302 includes a groove 1304 configured to receive used floss 106. The groove 1304 includes a jamb angle for gripping the used floss 106. The take-up reel 1302 further includes a ratchet 1306 and a pawl 1308 for resisting rotation in one direction. The take-up reel 1302 includes knurling 1310 around an upper edge. A user may engage the knurled edge 1310, e.g., using a thumb or finger, for applying friction to rotate the take-up reel 1302. Thus, the take-up reel 1302 may be rotated for advancing the floss 102-106 while ratchet 1306 and pawl 1308 maintain tension on the floss 102-106 by preventing reverse rotation of the take-up reel. The groove 1304, the knurled edge 1310, and the ratchet 1306 and pawl 1308 mechanism may be used together or in various combinations for the flosser 100, flosser 1100, and/or the flosser 1200. The groove 1304, the knurled edge 1310, and the ratchet 1306 and pawl 1308 mechanism may be used together or in various combinations for a source spool on the flosser 100, flosser 1100, and/or the flosser 1200.

Figure 14:
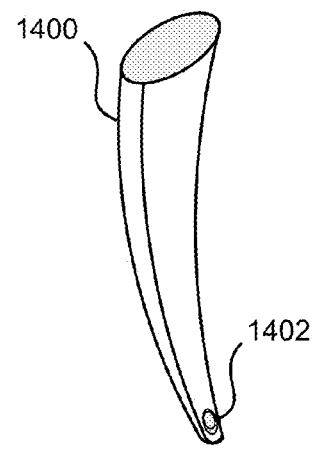
FIG. 14 illustrates an alternative embodiment of a projection.

FIG. 14 illustrates an alternative embodiment of a projection 1400. The projection 1400 includes an aperture 1402 for guiding floss. The projection 1400 comprises an oval cross section and a curve. The projection 1400 may be used on the head 120 and/or the head 1220, in the place of the projection 122, projection 123 and/or tube 124.

The source of floss has been described as a spool, e.g., source spool 112. However, in various embodiments, the source of floss includes a bundle of floss, a ball of floss, a roll of floss, a skein of floss and/or the like.

Figure 15:
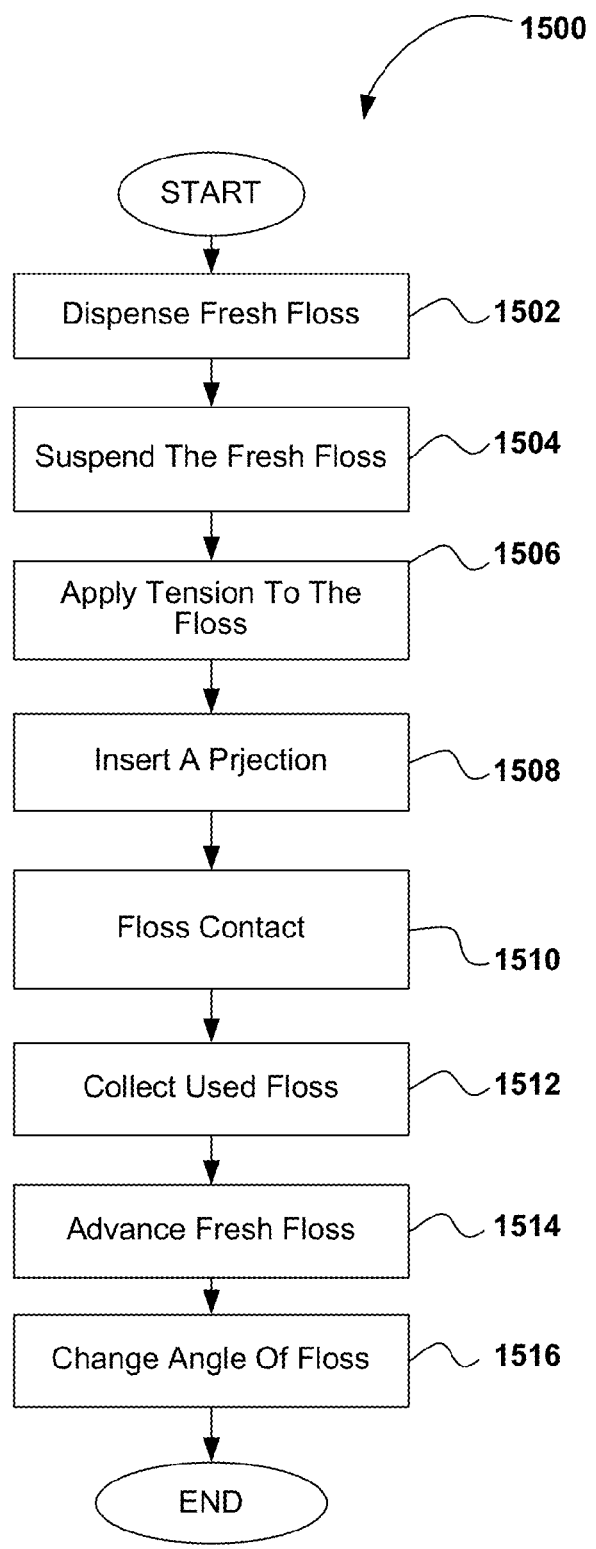
FIG. 15 is a flow diagram of an exemplary process for flossing teeth.

FIG. 15 is a flow diagram of an exemplary process 1500 for flossing teeth. In step 1502, fresh floss is dispensed from an elongated handle. In step 1504, the fresh floss is suspended at an angle to the elongate handle between a pair of projections. In step 1506, a tension is applied to the suspended fresh floss. In step 1508, one of the projections is inserted between the teeth and a wire brace. In step 1510, the contact is flossed using the suspended fresh floss. In step 1512, used floss is collected while maintaining the tension on the suspended floss. In step 1514, fresh floss is advanced into suspension. In step 1516, the angle of the floss with respect to the elongated handle is changed.

The embodiments discussed herein are illustrative. As these embodiments are described with reference to illustrations, various modifications or adaptations of the methods and/or specific structures described may become apparent to persons of ordinary skill in the art. Various features and aspects of the above described present invention may be used individually or jointly. Features in each of the various illustrations may be combined with features in other illustrations or used individually for illustrating the present invention. All such modifications, adaptations, or variations that rely upon the teachings of the embodiments, and through which these teachings have advanced the art, are considered to be within the spirit and scope of the present application. Hence, these descriptions and drawings should not be considered in a limiting sense, as it is understood that the present application is in no way limited to only the embodiments illustrated.

What is claimed is:

1. A flosser for cleaning contacts between two teeth attached to a wire brace, the flosser comprising:
   a handle;
   a head coupled to the handle at an angle;
   a first floss support coupled to the head and extending away from a plane formed by the angle between the head and the handle;
   a second floss support extending from the head about parallel to the first floss support and including an aperture for supporting floss suspended between the first floss support and the second floss support, the second floss support shaped for insertion of the aperture between the wire brace and the two teeth while the suspended floss cleans the contact between the two teeth;

an aperture disposed in the head and spaced from the second floss support to suspend a portion of the floss at an acute angle with respect to the second support for cleaning the wire brace;

a source spool disposed on the handle for dispensing fresh floss, the aperture sized for feeding the fresh floss into suspension between the first and second floss support; and a take-up spool disposed on the handle for receiving used floss from the first floss support and for advancing the fresh floss through the aperture, the take-up spool and the source spool configured to apply tension to the suspended floss.

2. The flosser of claim 1, wherein the first floss support is sized for insertion between the wire brace and the two teeth while the suspended floss cleans the contact between the two teeth.

3. The flosser of claim 1, wherein the take-up spool includes a groove configured for receiving a length of floss across a diameter of the spool, the groove having a jamb angle for gripping the floss.

4. The flosser of claim 1, wherein the take-up spool includes a ratchet for holding tension on the suspended floss.

5. The flosser of claim 1, wherein the first floss support includes a channel.

6. The flosser of claim 1, further comprising an anti-microbial agent disposed in the suspended floss.

7. The flosser of claim 6, wherein the antimicrobial agent includes chlorhexidine guconate.

8. A flosser comprising:

an elongated handle;

an articulating head coupled to the handle at a pivot;

a first detent to hold the articulating head at a first angle with respect to an axis of the handle and a second detent to hold the head at a second angle with respect to the axis;

a first and second projection extending from the head and configured for suspending floss, the first projection sized to insert between a tooth and a wire mounted on the tooth; and an aperture disposed in the articulated head and spaced from the second projection to suspend a portion of the floss at an acute angle with respect to the second support for cleaning the wire mounted on the tooth.

9. The flosser of claim 8, wherein the first angle and the second angle are opposite the axis of the handle.

10. The flosser of claim 8, further comprising a supply of fresh floss attached to the handle, the supply configured to feed the fresh floss under tension to the projections.

11. The flosser of claim 10, wherein the first projection includes an aperture sized for allowing passage of the fresh floss into suspension between the projections.

12. The flosser of claim 10, further comprising a take-up reel configured to receive used floss from the projections and oppose the supply of floss for applying the tension to the floss suspended between the first and second projections.

13. The flosser of claim 12, wherein the take-up reel includes a ratchet.

14. The flosser of claim 8, wherein the head includes a guide positioned for suspending the fresh floss between the first projection and the wire at an angle extending away from the tooth for flossing surfaces of braces.

* * * * *